(12) United States Patent
Katayama

(10) Patent No.: US 10,570,279 B2
(45) Date of Patent: Feb. 25, 2020

(54) POLYPROPYLENE RESIN COMPOSITION AND MOLDED BODY FOR MEDICAL USE, WHICH USES SAME

(71) Applicant: SUMITOMO CHEMICAL COMPANY, LIMITED, Tokyo (JP)

(72) Inventor: Shingo Katayama, Ichihara (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 78 days.

(21) Appl. No.: 15/743,350

(22) PCT Filed: Jul. 11, 2016

(86) PCT No.: PCT/JP2016/070471
§ 371 (c)(1),
(2) Date: Jan. 10, 2018

(87) PCT Pub. No.: WO2017/014096
PCT Pub. Date: Jan. 26, 2017

(65) Prior Publication Data
US 2018/0201772 A1    Jul. 19, 2018

(30) Foreign Application Priority Data
Jul. 17, 2015    (JP) .................... 2015-143002

(51) Int. Cl.
| | | |
|---|---|---|
| *C08L 23/14* | (2006.01) | |
| *C08L 23/12* | (2006.01) | |
| *A61L 31/04* | (2006.01) | |
| *C08J 3/22* | (2006.01) | |
| *C08L 53/02* | (2006.01) | |
| *A61M 5/31* | (2006.01) | |
| *C08L 25/10* | (2006.01) | |
| *C08L 23/10* | (2006.01) | |
| *A61M 1/14* | (2006.01) | |
| *C08L 35/00* | (2006.01) | |
| *C08K 5/521* | (2006.01) | |
| *C08K 5/3435* | (2006.01) | |
| *C08K 5/00* | (2006.01) | |
| *A61M 1/16* | (2006.01) | |

(52) U.S. Cl.
CPC ............ *C08L 23/14* (2013.01); *A61L 31/041* (2013.01); *A61M 1/14* (2013.01); *A61M 5/31* (2013.01); *C08K 5/3435* (2013.01); *C08K 5/521* (2013.01); *C08L 23/10* (2013.01); *C08L 23/12* (2013.01); *C08L 25/10* (2013.01); *C08L 35/00* (2013.01); *C08L 53/02* (2013.01); *A61M 1/1621* (2014.02); *A61M 5/3129* (2013.01); *C08K 5/0083* (2013.01); *C08L 2201/08* (2013.01); *C08L 2203/02* (2013.01); *C08L 2205/03* (2013.01)

(58) Field of Classification Search
CPC .......... C08L 23/14; C08L 23/12; A61L 31/04; C08J 3/22
USPC ......................................................... 524/117
See application file for complete search history.

(56) References Cited

U.S. PATENT DOCUMENTS

| | | |
|---|---|---|
| 2010/0292371 A1 | 11/2010 | Maruyama et al. |
| 2011/0129627 A1 | 6/2011 | Schedenig et al. |
| 2013/0189462 A1 | 7/2013 | Hama et al. |
| 2014/0045985 A1* | 2/2014 | Nagasima ............... C08L 23/12 524/441 |
| 2015/0152254 A1 | 6/2015 | Shimano |

FOREIGN PATENT DOCUMENTS

| | | |
|---|---|---|
| CN | 101602877 A | 12/2009 |
| CN | 102112541 A | 6/2011 |
| CN | 103214729 A | 7/2013 |
| CN | 103502352 A | 1/2014 |
| CN | 104672625 A | 6/2015 |
| JP | 09-087446 A | 3/1997 |
| JP | H09-296085 A | 11/1997 |
| JP | H10-168243 A | 6/1998 |
| JP | 2002097322 A | 4/2002 |
| JP | 2006225468 A | 8/2006 |
| JP | 2009-082698 A | 4/2009 |
| JP | 2009-167407 A | 7/2009 |
| JP | 2012-201793 A | 10/2012 |
| JP | 2013-173923 A | 9/2013 |
| JP | 2013-216814 A | 10/2013 |
| JP | 2015-044979 A | 3/2015 |
| JP | 2015-127405 A | 7/2015 |

OTHER PUBLICATIONS

International Search Report for PCT/JP2016/070471 dated Sep. 6, 2016 [PCT/ISA/210].
Communication dated Jan. 3, 2019 from the European Patent Office in application No. 16827657.4.
Notice of Reasons for Rejection dated Jun. 4, 2019 issued by the Japanese Patent Office in counterpart Application No. 2015-143002.
International Preliminary Report on Patentability with the translation of Written Opinion dated Feb. 1, 2018, issued by the International Bureau in International Application No. PCT/JP2016/070471.

(Continued)

*Primary Examiner* — Deve V Hall
(74) *Attorney, Agent, or Firm* — Sughrue Mion, PLLC

(57) ABSTRACT

Disclosed is a polypropylene resin composition comprising (A) a propylene-based polymer, (B) a styrene-based elastomer, (C) a hindered amine light stabilizer having a secondary amino group, and (D) a nucleating agent containing an aromatic phosphate metal salt. The content of the propylene-based polymer is more than 90% by mass and 99% by mass or less, and the content of the styrene-based elastomer is 1% by mass or more and less than 10% by mass.

7 Claims, 2 Drawing Sheets

(56) References Cited

OTHER PUBLICATIONS

Communication dated Jan. 7, 2020 from Japanese Patent Office in counterpart JP Application No. 2015-143002.
Communication dated Oct. 22, 2019, from National Intellectual Property Administration, P.R. China in counterpart Application No. 201680041899.9.

* cited by examiner

POLYPROPYLENE RESIN COMPOSITION AND MOLDED BODY FOR MEDICAL USE, WHICH USES SAME

CROSS REFERENCE TO RELATED APPLICATIONS

This application is a National Stage of International Application No. PCT/JP2016/070471 filed Jul. 11, 2016, claiming priority based on Japanese Patent Application No. 2015-143002 filed Jul. 17, 2015, the contents of all of which are incorporated herein by reference in their entirety.

TECHNICAL FIELD

The present invention relates to a polypropylene resin composition, and a molded body for medical use using the same. The molded body for medical use can be used as a barrel for syringes or a housing for dialyzers, for example.

BACKGROUND ART

As resin materials for molded bodies for medical use such as barrels for syringes and housings for dialyzers, materials such as cycloolefin polymer (COP), cycloolefin copolymer (COC), and polycarbonate (PC) have been generally used. However, application of polypropylene resin compositions containing polypropylene-based polymers, which are cheaper materials, to the field of molded bodies for medical use has also been examined (for example, Patent Literatures 1 and 2).

CITATION LIST

Patent Literature

Patent Literature 1: Japanese Unexamined Patent Publication No. 2009-82698
Patent Literature 2: Japanese Unexamined Patent Publication No. 2015-44979

SUMMARY OF INVENTION

Technical Problem

Such molded bodies of polypropylene resin compositions for medical use are desired to maintain a small amount of extractable substances and good mechanical properties even after sterilization with radiation rays.

Solution to Problem

One aspect of the present invention relates to a polypropylene resin composition comprising (A) a propylene-based polymer, (B) a styrene-based elastomer, (C) a hindered amine light stabilizer having a secondary amino group as a hindered amino group, and (D) a nucleating agent containing an aromatic phosphate metal salt. The content of the propylene-based polymer is 90% by mass or more and 99% by mass or less relative to the total amount of the propylene-based polymer and the styrene-based elastomer, and the content of the styrene-based elastomer is 1% by mass or more and 10% by mass or less relative to the total amount of the propylene-based polymer and the styrene-based elastomer.

The molded body obtained from the polypropylene resin composition can maintain a small amount of extractable substances and good mechanical properties even after sterilization with radiation rays.

The hindered amine light stabilizer may be a polymer containing a repeating structural unit having a secondary amino group. Using such a polymer, advantageous effects of the present invention are more remarkably exhibited.

The polypropylene resin composition may further comprise (E) a hydroxylamine compound having a hydroxylamino group. When the polypropylene resin composition contains a hydroxylamine compound, there can be exhibited more remarkable effects of maintaining a small amount of extractable substances and good mechanical properties even after sterilization with radiation rays.

The content of the monomer unit derived from ethylene in the propylene-based polymer may be less than 5% by mass based on the mass of the propylene-based polymer. When the content of the monomer unit derived from ethylene is small, a molded body having an excellent balance between resistance against radiation rays and heat resistance is more readily obtained.

In another aspect, the present invention relates to a molded body for medical use consisting of the polypropylene resin composition. Further another aspect of the present invention provides a syringe comprising a barrel having such a molded body for medical use, and a dialyzer comprising a housing having such a molded body for medical use.

Advantageous Effects of Invention

As to the molded body of the polypropylene resin composition for medical use, a small amount of extractable substances and good mechanical properties can be maintained even after sterilization with radiation rays.

DESCRIPTION OF EMBODIMENTS

Figure 1:
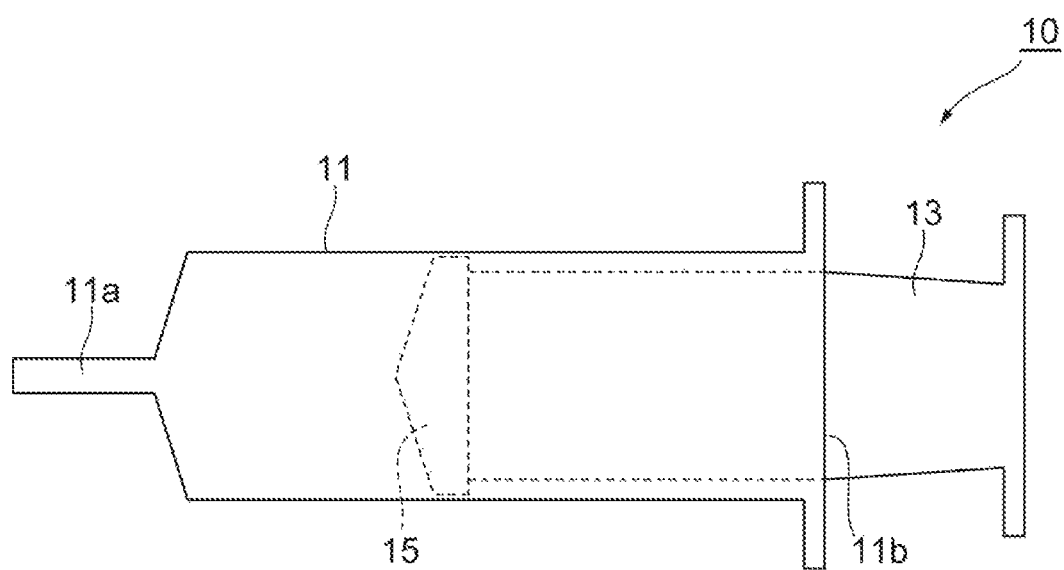
FIG. 1 is a plan view illustrating one embodiment of a syringe.

Hereinafter, suitable embodiments of the present invention will be described in detail. It should be noted that the present invention will not be limited to these embodiments below. Components described below can be arbitrarily combined. For example, upper limit values and lower limit values exemplified related to ranges of numeric values can be arbitrarily combined.

1. Polypropylene Resin Composition

The polypropylene resin composition according to one embodiment contains (A) a propylene-based polymer, (B) a styrene-based elastomer, (C) a hindered amine light stabilizer having a secondary amino group as a hindered amino group, and (D) a nucleating agent containing an aromatic phosphate metal salt.

(A) Propylene-Based Polymer

The polypropylene resin composition according to one embodiment contains one or more propylene-based polymers. The propylene-based polymer is a polymer mainly composed of a monomer unit derived from propylene. The propylene-based polymer may be a homopolymer of propylene, or may be a copolymer of propylene and another comonomer. The propylene-based polymer may have crystallinity.

The content of the monomer unit derived from propylene in the propylene-based polymer may be 85% by mass or more, 90% by mass or more, or 95% by mass or more based on the mass of the propylene-based polymer. The upper limit of the content of the monomer unit derived from propylene is 100% by mass.

The comonomer constituting the propylene-based polymer may be α-olefin, for example. The α-olefin may be ethylene and/or α-olefin having 4 to 20 carbon atoms. Specific examples of the α-olefin having 4 to 20 carbon atoms include butene-1, pentene-1, hexene-1, 4-methylpentene-1, heptene-1, octene-1, and decene-1. The α-olefin having 4 to 20 carbon atoms may be at least one selected from butene-1, hexene-1, and octene-1.

Examples of copolymers of propylene and ethylene and/or α-olefin having 4 to 20 carbon atoms include propylene-ethylene copolymers, propylene-butene-1 copolymers, propylene-ethylene-butene-1 copolymers, propylene-hexene-1 copolymers, and propylene-ethylene-hexene-1 copolymers. The propylene-based polymer may be a propylene-ethylene copolymer, a propylene-butene-1 copolymer, or a propylene-ethylene-butene-1 copolymer.

The content of the monomer unit derived from the comonomer in the propylene-based polymer is usually 0% by mass or more and less than 15% by mass based on the mass of the propylene-based polymer, and may be less than 10% by mass, or less than 5% by mass in view of the rigidity and heat resistance of the molded body. The content may be 0.01% by mass or more.

The melt flow rate (MFR) at 230° C. of the propylene-based polymer may be 0.5 to 500 g/10 minutes, 10 to 100 g/10 minutes, 22 to 80 g/10 minutes, or 25 to 50 g/10 minutes. When the propylene-based polymer has an appropriate melt flow rate, good fluidity is readily obtained in the case where the resin composition is injection molded. From the same viewpoint, the limiting viscosity [η] of the propylene-based polymer may be 0.5 to 4 dl/g, 1 to 3 dl/g, or 1 to 2 dl/g.

The content of the propylene-based polymer in the polypropylene resin composition is usually 90% by mass or more and 99% by mass or less relative to the total amount of the propylene-based polymer and the styrene-based elastomer. Thereby, a molded body which can maintain a small amount of extractable substances and good mechanical properties even after sterilization with radiation rays can be obtained. From the same viewpoint, the content of the propylene-based polymer may be 92% by mass or more or 94% by mass or more, and may be 98% by mass or less or 97% by mass or less.

The propylene-based polymer can be produced by polymerizing the monomer(s) including propylene by a usual method. The propylene-based polymer can be obtained, for example, through polymerization by slurry polymerization, solution polymerization, liquid phase polymerization using an olefin monomer as a medium, or gaseous phase polymerization in the presence of a solid catalyst for stereoregular polymerization containing a titanium atom and an electron donating compound according to Japanese Unexamined Patent Publication No. H7-216017. The proportion of the electron donating compound used there is usually 0.01 to 500 mol relative to 1 mol of titanium atom contained in the solid catalyst, and may be 0.01 to 100 mol, or 0.01 to 50 mol.

(B) Styrene-Based Elastomer

The polypropylene resin composition according to one embodiment contains one or more kinds of styrene-based elastomers. The styrene-based elastomer is an elastomer containing styrene as a monomer unit. The proportion of the monomer unit derived from styrene in the styrene-based elastomer may be 5% by mass or more and 80% by mass or less based on the total mass of the styrene-based elastomer. The styrene-based elastomer may be a hydrogenated product, in which part or all of unsaturated bonds derived from monomer alkadiene or the like (usually, excluding the unsaturated bond of the benzene ring derived from styrene) have been converted into saturated bonds by hydrogenation. The heat resistance tends to be improved by hydrogenation.

The styrene-based elastomer may be a block copolymer composed of a polystyrene block and a polyolefin block consisting of monomer units derived from α-olefin having 2 to 10 carbon atoms and/or alkadiene having 4 to 10 carbon atoms, or a hydrogenated product thereof, for example. In view of the compatibility with the propylene-based polymer and impact resistance, the polyolefin block may contain one or more kinds of α-olefins selected from ethylene, propylene, butene, isoprene, and butadiene and/or alkadiene as monomer units.

The styrene-based elastomer may be a diblock type copolymer consisting of a polystyrene block and a polyolefin block bonded thereto, or may be a triblock type copolymer consisting of a polystyrene block disposed at both terminals and a polyolefin block disposed therebetween. The triblock type copolymer can contribute to an improvement in impact resistance of the molded body.

The proportion of the polyolefin block in the block copolymer as the styrene-based elastomer may be 20% by mass or more, 60% by mass or more, or 75% by mass or more based on the mass of the block copolymer, and may be 95% by mass or less. When the styrene-based elastomer contains the polyolefin block in an appropriate proportion, a molded body having good properties in transparency, impact resistance, rigidity, and stickiness is readily obtained.

The melt flow rate (MFR: 230° C., 2.16 kg) of the styrene-based elastomer may be 1 to 50 g/10 minutes. If the MFR is high, an effect of improving the impact resistance tends to be reduced, and excess stickiness tends to readily occur. If the MFR is low, the transparency of the molded body may be reduced because the dispersibility of the styrene-based elastomer in the resin composition is reduced.

The content of the styrene-based elastomer in the polypropylene resin composition is typically 1% by mass or more and 10% by mass or less relative to the total amount of the propylene-based polymer and the styrene-based elastomer. Thereby, a molded body which can maintain a small amount of extractable substances and good mechanical properties even after sterilization with radiation rays can be obtained. From the same viewpoint, the content of the styrene-based elastomer may be 2% by mass or more or 3% by mass or more, and may be 6% by mass or less or 8% by mass or less.

The styrene-based elastomer can be produced by a usual method such as living anionic polymerization or living cationic polymerization. The styrene-based elastomer is also available as a commercial product. Examples of the commercial product include a trade name "Kraton" manufactured by Kraton Corporation, a trade name "Tuftec" manufactured by Asahi Kasei Corporation, trade names "Septon" and "Hybrar" manufactured by Kuraray Co., Ltd., and a trade name "Dynaron" manufactured by JSR Corporation.

(C) Hindered Amine Light Stabilizer

The polypropylene resin composition according to one embodiment contains one or more kinds of hindered amine light stabilizers having a secondary amino group as a hindered amino group.

The acid dissociation constant (pKa) of the secondary amino group which the hindered amine light stabilizer has may be less than 8 or 7 or less. Thereby, a higher effect is obtained in terms of a reduction in extractable substances after sterilization with radiation rays. The acid dissociation constant (pKa) is a value determined by titration.

The molecular weight of the hindered amine light stabilizer may be 1000 or more. When the molecular weight of the hindered amine light stabilizer is large, it is advantageous in resistance against radiation rays, and a reduction in extractable substances in the molded body. From the same viewpoint, the molecular weight of the hindered amine light stabilizer may be 1500 or more or 2000 or more. The upper limit of the molecular weight of the hindered amine light stabilizer is not particularly limited, and may be 10000 or less, for example. The molecular weight here is a weight average molecular weight. The weight average molecular weight may be a value determined in terms of standard polystyrene by gel permeation chromatography (GPC).

The hindered amine light stabilizer has a 2,2,6,6-tetraalkyl-4-piperidyl group represented by the following formula (I), for example. $R^1$, $R^2$, $R^3$, and $R^4$ each independently represent an alkyl group having 1 to 4 carbon atoms. $R^1$, $R^2$, $R^3$, and $R^4$ may be a methyl group. In view of the resistance against radiation rays, the 2,2,6,6-tetraalkyl-4-piperidyl group in formula (I) may bond to an oxygen atom or a nitrogen atom:

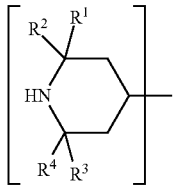
(I)

The hindered amine light stabilizer may be a polymer containing a repeating structural unit having a secondary amino group. The repeating structural unit having a secondary amino group may be a divalent structural unit represented by the following formula (II), for example:

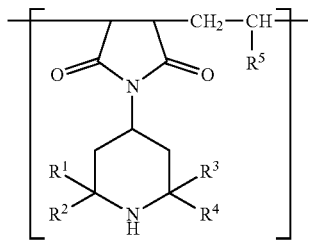
(II)

In formula (II), $R^1$, $R^2$, $R^3$, and $R^4$ are the same as those in $R^1$, $R^2$, $R^3$, and $R^4$ in formula (I). $R^5$ represents an alkyl group having 10 to 30 carbon atoms. $R^5$ may be an alkyl group having 14 to 28 carbon atoms, 16 to 26 carbon atoms, or 18 to 22 carbon atoms. The alkyl group may have any one of linear, branched, cyclic structures, and combinations thereof. $R^5$ may be a linear alkyl group.

In view of a reduction in extractable substances and maintenance of good mechanical properties after sterilization with radiation rays, the content of the hindered amine light stabilizer in the polypropylene resin composition may be 0.001% by mass or more, 0.05% by mass or more, or 0.1% by mass or more, and may be 1% by mass or less, 0.5% by mass or less, or 0.3% by mass or less, based on the total amount of the propylene-based polymer and the styrene-based elastomer.

The polypropylene resin composition may further contain a light stabilizer other than the hindered amine light stabilizers having a secondary amino group listed above.

(D) Nucleating Agent

The polypropylene resin composition contains a nucleating agent containing one or more kinds of aromatic phosphate metal salts. The nucleating agent typically has a particulate form. The aromatic phosphate metal salt is a salt formed from an aromatic phosphate and a metal, and may be an alkali metal salt, an alkaline earth metal salt, or an aluminum salt, for example. Examples of the alkali metal salts include lithium salts, sodium salts, and potassium salts. Examples of the alkaline earth metal salts include beryllium salts, calcium salts, magnesium salts, strontium salts, and barium salts. In view of an effect of high extraction resistance, the aromatic phosphate metal salt may be an aluminum salt, a lithium salt, or a sodium salt, or may be a lithium salt.

The aromatic phosphate metal salt is represented by the following formula (20), for example:

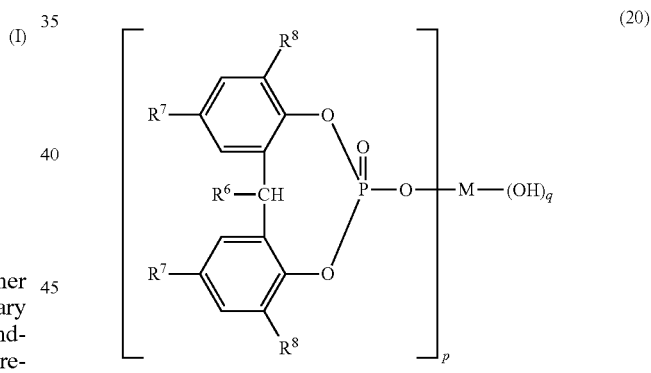
(20)

In formula (20), $R^6$ represents a hydrogen atom or an alkyl group having 1 to 4 carbon atoms, $R^7$ and $R^8$ each independently represent a hydrogen atom, an alkyl group having 1 to 12 carbon atoms, a cycloalkyl group having 3 to 12 carbon atoms, an aryl group having 6 to 12 carbon atoms, or an aralkyl group having 7 to 12 carbon atoms, and M represents an alkali metal atom, an alkaline earth metal atom, or an aluminum atom. When M is an alkali metal atom, p is 1 and q is 0; when M is an alkaline earth metal atom, p is 2 and q is 0; and when M is an aluminum atom, p is 1 or 2 and q is 3−p.

Examples of the alkyl group having 1 to 4 carbon atoms represented by $R^6$ include a methyl group, an ethyl group, a propyl group, an iso-propyl group, an n-butyl group, a sec-butyl group, and an iso-butyl group. Examples of the alkyl group having 1 to 12 carbon atoms represented by $R^7$ or $R^8$ include a methyl group, an ethyl group, a propyl group, an iso-propyl group, an n-butyl group, a sec-butyl group, a tert-butyl group, an amyl group, a tert-amyl group, a hexyl group, a heptyl group, an octyl group, an iso-octyl group, a tert-octyl group, a 2-ethylhexyl group, a nonyl group, an iso-nonyl group, a decyl group, an iso-decyl group, an undecyl group, a dodecyl group, and a tert-dodecyl group. $R^7$ and $R^8$ both may be a tert-butyl group.

Examples of the alkali metal atom represented by M include lithium, sodium, and potassium. Examples of the alkaline earth metal atom represented by M include beryllium, calcium, magnesium, strontium, and barium.

Specific examples of the salts of the aromatic phosphate and Al represented by formula (20) where M is an aluminum atom include hydroxyaluminum-bis[2,2'-methylene-bis(4,6-dimethylphenyl)phosphate], hydroxyaluminum-bis[2,2'-ethylidene-bis(4,6-dimethylphenyl)phosphate], hydroxyaluminum-bis[2,2'-methylene-bis(4,6-diethylphenyl)phosphate], hydroxyaluminum-bis[2,2'-ethylidene-bis(4,6-diethylphenyl)phosphate], hydroxyaluminum-bis[2,2'-methylene-bis(4,6-di-tert-butylphenyl)phosphate], hydroxyaluminum-bis[2,2'-ethylidene-bis(4,6-di-tert-butylphenyl)phosphate], hydroxyaluminum-bis[2,2'-methylene-bis(4-methyl-6-t-butylphenyl)phosphate], hydroxyaluminum-bis[2,2'-ethylidene-bis(4-methyl-6-t-butylphenyl)phosphate], hydroxyaluminum-bis[2,2'-methylene-bis(4-ethyl-6-tert-butylphenyl)phosphate], hydroxyaluminum-bis[2,2'-ethylidene-bis(4-ethyl-6-tert-butylphenyl)phosphate], hydroxyaluminum-bis[2,2'-methylene-bis(4-iso-propyl-6-tert-butylphenyl)phosphate], and hydroxyaluminum-bis[2,2'-ethylidene-bis(4-iso-propyl-6-tert-butylphenyl)phosphate]. Among these, hydroxyaluminum-bis[2,2'-methylene-bis(4,6-di-tert-butylphenyl)phosphate] or hydroxyaluminum-bis[2,2'-ethylidene-bis(4,6-di-tert-butylphenyl)phosphate] may be selected, or hydroxyaluminum-bis[2,2'-methylene-bis(4,6-di-tert-butylphenyl)phosphate] may be selected. These can be used singly or in combinations of two or more.

The aromatic phosphate metal salt is available as a commercial product. Examples of the commercial product include a mixture of hydroxyaluminum-bis[2,2'-methylene-bis(4,6-di-tert-butylphenyl)phosphate] and an aliphatic monocarboxylic acid lithium salt having 8 to 20 carbon atoms (manufactured by Adeka Corporation, trade name: Adekastab NA21).

In view of a reduction in extractable substances after sterilization with radiation rays, the content of the aromatic phosphate metal salt in the polypropylene resin composition may be 0.001% by mass or more, 0.005% by mass or more, 0.01% by mass or more, or 0.05% by mass or more, and may be 1% by mass or less, 0.995% by mass or less, 0.8% by mass or less, or 0.5% by mass or less, based on the total amount of the propylene-based polymer and the styrene-based elastomer.

(E) Hydroxylamine Compound

The polypropylene resin composition may further contain a hydroxylamine compound having a hydroxylamino group. Examples of the hydroxylamine compound include N,N-dialkylhydroxylamine such as N,N-dioctadecylhydroxylamine (HO—N($C_{18}H_{37}$)$_2$).

The content of the hydroxylamine compound in the polypropylene resin composition may be 0.01% by mass or more or 0.05% by mass or more, and may be 0.5% by mass or less or 0.3% by mass or less, based on the total amount of the propylene-based polymer and the styrene-based elastomer.

(Other Components)

The polypropylene resin composition may contain other components selected, for example, from an antioxidant, a neutralizer, a weather resistant agent, a flame retardant, an antistatic agent, a plasticizer, a lubricant, and a copper inhibitor when necessary.

(Production of Resin Composition)

The polypropylene resin composition can be obtained by melt kneading the propylene-based polymer, the styrene-based elastomer, the hindered amine light stabilizer, the aromatic phosphate metal salt, and other components when necessary by a usual method, for example. The polypropylene resin composition to be produced may have a form of pellets for molding. For example, a pelletized polypropylene resin composition can be obtained by a method including mixing raw materials with a mixer such as a tumbler mixer, a Henschel mixer, or a ribbon blender to prepare a mixture, and homogeneously melt kneading the mixture using a monoaxial extruder, a biaxial extruder, or a Banbury mixer.

2. Molded Body

The molded body obtained by molding the polypropylene resin composition has high resistance to sterilization treatments such as sterilization with radiation rays such as γ-rays, sterilization with electron beams, and sterilization with high pressurized steam, and therefore is useful as a molded body for medical use contacting a variety of drugs during use. Examples of the molded body for medical use include barrels for syringes, and housings for dialyzers. The syringes may be disposable syringes, or may be pre-filled syringes containing a chemical solution preliminarily filled.

FIG. 1 is a plan view illustrating one embodiment of the syringe. A syringe 10 illustrated in FIG. 1 includes a barrel 11, a plunger 13, and a gasket 15 attached to the distal end of the plunger 13. The barrel 11 has a mouth 11a formed at the distal end, and a proximal end 11b forming an opening, and the plunger 13 is inserted into the barrel 11 from the opening of the proximal end 11b.

The barrel 11 is a molded body of the polypropylene resin composition. The thickness and size of the barrel 11 are appropriately set in the usual range. The plunger 13 and the gasket 15 can be selected from those usually used in the field of the syringe.

Figure 2:
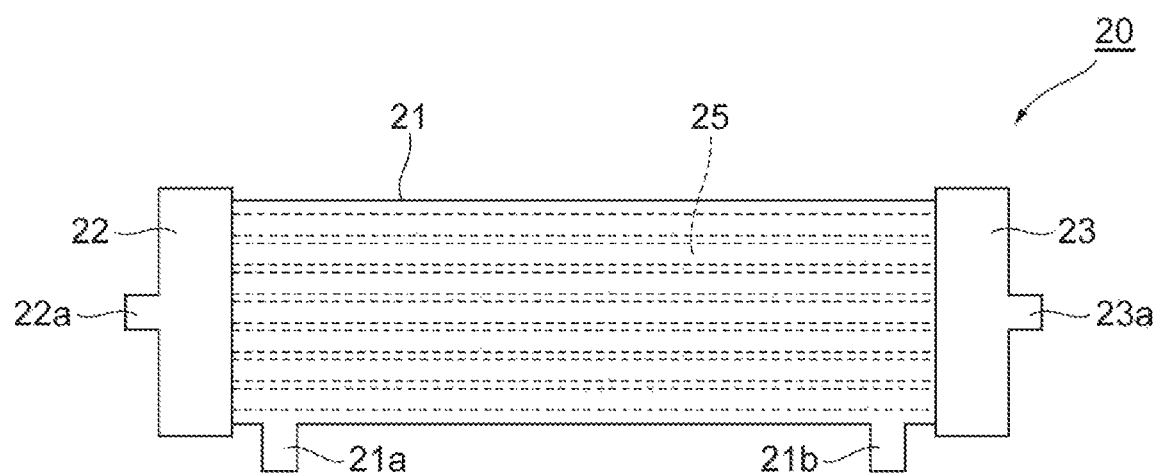
FIG. 2 is a plan view illustrating one embodiment of a dialyzer.

FIG. 2 is a plan view illustrating one embodiment of the dialyzer. A dialyzer 20 illustrated in FIG. 2 includes a cylindrical housing 21, a plurality of hollow fiber membranes 25 accommodated in the housing 21 while being aligned in the longitudinal direction of the housing 21, and headers 22 and 23 attached to both ends of the housing 21. The housing 21 has a dialysis solution outlet 21a disposed at one end and a dialysis solution inlet 21b disposed at the other end. One header 22 has a blood inlet 22a and the other header 23 has a blood outlet 23a.

The housing 21 is a molded body of the polypropylene resin composition. During use of the dialyzer 20, the inside of the housing 21 is filled with a dialysis solution introduced from the dialysis solution inlet 21b. The thickness and size of the housing 21 are appropriately set in the usual range. The hollow fiber membranes 25 and the headers 22 and 23 can be selected from those usually used in the field of the dialyzer for dialysis.

EXAMPLES

Hereinafter, the present invention will be more specifically described by way of Examples. It should be noted that the present invention will not be limited to these Examples.

1. Raw Materials: The following raw materials were used in Examples and Comparative Examples.

(A) Propylene-Based Polymer

According to the method described in Example 1 in Japanese Unexamined Patent Publication No. H7-216017, a solid polymerization catalyst for α-olefin polymerization was prepared. Propylene and ethylene were subjected to gaseous phase polymerization in the presence of the solid polymerization catalyst to obtain a powdery propylene-ethylene copolymer. The properties of the resulting propylene-ethylene copolymer were measured by the methods described later, the melt flow rate was 25 g/10 minutes, the content of the monomer unit derived from ethylene was 2.5% by mass, and the melting point was 144.1° C.

(B) Styrene-Based Elastomer

A hydrogenated product of the styrene-isoprene-butadiene block copolymer (Hybrar 7311F, manufactured by Kuraray Co., Ltd., content of monomer unit derived from styrene: 12% by mass)

(C) Hindered Amine Light Stabilizer

A copolymer of N-(2,2,6,6,-tetramethyl-4-piperidine)maleic acid imide and α-olefin (C20-24) (copolymer represented by formula (IIa) where n represents an integer of 2 or more, Uvinul 5050 H, manufactured by BASF Japan Ltd., molecular weight: 3500, pKa: 7.0)

$$\left[ \begin{array}{c} \text{structure (IIa)} \end{array} \right]_n \quad (\text{IIa})$$

(D) Nucleating Agent

Aromatic Phosphate Metal Salt

A mixture of hydroxyaluminum-bis[2,2-methylene-bis(4,6-di-tert-butylphenyl)phosphate] (compound represented by formula (20a)) and an aliphatic monocarboxylic acid lithium salt having 8 to 20 carbon atoms (ADEKASTAB NA-21, manufactured by Adeka Corporation)

$$\left[ \begin{array}{c} \text{structure (20a)} \end{array} \right]_2 \quad (20a)$$

Sorbitol-Based 1,2,3-Trideoxy-4,6:5,7-bis-[(4-propylphenyl)methylene]-nonitol (Millad NX8000J, manufactured by Milliken Chemical)

(E) Antioxidant

A mixture of 50% by mass of N,N-dioctadecylhydroxylamine and 50% by mass of tris(2,4-di-tert-butylphenyl) phosphite (Irgastab FS301, manufactured by BASF Japan Ltd.)

(Neutralizer)

Magnesium-aluminum-hydroxide-carbonate (DHT-4C, manufactured by Kyowa Chemical Industry Co., Ltd.)

2. Test Methods (1) Content of Monomer Unit in Propylene-Based Polymer

The IR spectrum of the propylene-based polymer (propylene-ethylene random copolymer) was measured. From the resulting IR spectrum data, the content of the monomer unit derived from ethylene (unit: % by mass) was determined according to "(i) Method for random copolymers" described in p. 616 of Koubunshi Bunseki Handobukku (Polymer analysis handbook) (1995, published by Kinokuniya Company Ltd.).

Next, the content of the monomer unit derived from ethylene was substituted into the following expression to calculate the content of the monomer unit derived from propylene in the propylene-based polymer.

Content of monomer unit derived from propylene (% by mass)=100(% by mass)–content of the monomer unit derived from ethylene (% by mass)

(2) Melt Flow Rate (MFR, Unit: g/10 Minutes)

The melt flow rate was measured according to the method in Condition 14 of JIS K 7210 under conditions of a temperature of 230° C. and a load of 21.18 N.

(3) Melting Point (Unit: ° C.)

The melting point of the propylene-based polymer was measured based on ISO11357-3:98 using a differential scanning calorimeter (manufactured by TA Instruments—Waters LLC, DSC Q100 V9.9 Build 303).

(4) Evaluation of Polypropylene Resin Composition (4-1) Production of Pellets for Extractable Substance Test The raw materials in a composition (parts by mass) shown in Table 1 were dry blended using a Henschel mixer under a nitrogen atmosphere. The resulting mixture was melt kneaded with a biaxial kneading extruder (manufactured by TECHNOVEL CORPORATION, screw diameter: 20 mm φ) under a nitrogen atmosphere at 210° C. to obtain pellets of a polypropylene resin composition for Extractable Substance Test.

(4-2) Production of Test Piece for Tensile Test

The raw materials in a composition (parts by mass) shown in Table 1 were dry blended using a Henschel mixer under a nitrogen atmosphere. The resulting mixture was melt kneaded with a monoaxial extrusion granulator (manufactured by TANABE PLASTICS MACHINERY CO., LTD., screw diameter: 40 mm φ, VS40-28 type) under a nitrogen atmosphere at 210° C. to obtain pellets of the polypropylene resin composition. The resulting pellets were injection molded using an IS100 EN-3A type injection molding machine (manufactured by TOSHIBA MACHINE CO., LTD.) at a molding temperature of 220° C. and a metal mold temperature of 50° C. to obtain a test piece for a tensile test (ADTM D638 Type 1, thickness: 3.2 mm).

(5) Irradiation with Gamma Ray

The pellet for Extractable Substance Test and the test piece for a tensile test were irradiated with a gamma ray under an air atmosphere at room temperature. The pellet for Extractable Substance Test was irradiated with a gamma ray at an average dose of 25 kGy, and the test piece for a tensile test was irradiated with a gamma ray at an average dose of 50 kGy.

(6) Extractable Substance Test (6-1) Adjustment of Test Solution 30 g of the pellet irradiated with a gamma ray at 25 kGy was washed with ultrapure water, and then was dried at room temperature. The pellet after drying was placed into a hard glass container; 300 mL of ultrapure water was added, and the container was sealed. The hard glass container containing the pellet and ultrapure water was heated at 121° C. for one hour using a high-pressure steam sterilizer, and then was left to stand to room temperature. The solution in the container after left to stand was used as a test solution. A hard glass container containing only ultrapure water was simultaneously treated to prepare a blank test solution.

(6-2) Measurement of Ultraviolet Absorption Spectrum

Based on the test method according to "(iv) Ultraviolet absorption spectrum" described in 1.2 Extractable Substance Test, 2.7.02 plastic pharmaceuticals container test method in The Japanese Pharmacopoeia 16th edition, the ultraviolet absorption spectra of the test solution and the blank test solution for control were measured, and the maximum absorbances were recorded in a wavelength range of 220 to 240 nm and in a wavelength range of 241 to 350 nm.

(7) Tensile Elongation at Break

Based on ASTM D638, the test piece irradiated with a gamma ray at 50 kGy was subjected to a tensile test under conditions of a tensile rate of 50 mm/min and a measurement temperature of 23° C. to measure the tensile elongation at break. This was defined as the initial tensile elongation at break.

The test piece irradiated with a gamma ray at 50 kGy was left to stand at 60° C. for one week or at 60° C. for two weeks for conditioning. Subsequently, the tensile elongation at break was measured by the same method as above to determine the tensile elongation at break after the accelerated aging test at 60° C. for one week and the tensile elongation at break after the accelerated aging test at 60° C. for two weeks. The retention rate of the tensile elongation at break was calculated by the following expression:

Retention rate of tensile elongation at break (%)={(tensile elongation at break after accelerated aging test)/(initial tensile elongation at break)}×100

TABLE 1

| | | Ex. 1 | Comp. Ex. 1 | Comp. Ex. 2 |
|---|---|---|---|---|
| Propylene-based polymer | Propylene-ethylene random copolymer | 98 | 100 | 98 |
| Styrene-based elastomer | Hydrogenated product of styrene-isoprene-butadiene block copolymer, Hybrar 7311F | 2 | | 2 |
| Hindered amine light stabilizer | Copolymer represented by formula (10) Uvinul5050H | 0.25 | 0.25 | 0.25 |
| Antioxidant | Hydroxylamine compound/phosphite-based Irgastab FS301 | 0.2 | 0.2 | 0.2 |
| Nucleating agent | Salt of aromatic phosphate and Al ADEKASTAB NA-21 | 0.2 | 0.2 | — |
| | Sorbitol-based Millad NX8000J | — | — | 0.2 |

TABLE 1-continued

| | | Ex. 1 | Comp. Ex. 1 | Comp. Ex. 2 |
|---|---|---|---|---|
| Neutralizer | DHT-4C | 0.05 | 0.05 | 0.05 |
| Extractable Substance Test (irradiation with gamma ray at 25 kGy) | Ultraviolet absorption spectrum 220-240 nm Maximum absorbance | 0.041 | 0.041 | 0.054 |
| | Ultraviolet absorption spectrum 241-350 nm Maximum absorbance | 0.024 | 0.026 | 0.043 |
| Tensile elongation at break (%) (irradiation with gamma ray at 50 kGy) | Initial | 178 | 171 | — |
| | After accelerated aging test at 60° C. for one week | 174 | 80 | — |
| | After accelerated aging test at 60° C. for two weeks | 140 | 28 | — |
| Retention rate of tensile elongation at break (%) (irradiation with gamma ray at 150 kGy) | After accelerated aging test at 60° C. for one week | 98 | 47 | — |
| | After accelerated aging test at 60° C. for two weeks | 79 | 16 | — |

In Extractable Substance Test in Example 1, because the maximum absorbance of the ultraviolet light absorption spectrum was low, it was confirmed that the amount of extractable substances from the pellets after irradiation with the gamma ray was small. The polypropylene resin composition in Example 1 did not exhibit a large reduction in tensile elongation at break even after irradiation with the gamma ray. From these results, it was confirmed that the molded body of the polypropylene resin composition according to the present invention can maintain a small amount of extractable substances and good mechanical properties even after sterilization with radiation rays.

REFERENCE SIGNS LIST

10: syringe, 11: barrel, 11a: mouth, 11b: proximal end, 13: plunger, 15: gasket, 20: dialyzer, 21: housing, 21a: dialysis solution outlet, 21b: dialysis solution inlet, 22, 23: header, 22a: blood inlet, 23a: blood outlet, 25: hollow fiber membrane.

The invention claimed is:

1. A polypropylene resin composition, comprising:
   (A) a propylene-based polymer;
   (B) a styrene-based elastomer;
   (C) a hindered amine light stabilizer having a secondary amino group as a hindered amino group; and
   (D) a nucleating agent containing an aromatic phosphate metal salt,
   wherein a content of the propylene-based polymer is 90% by mass or more and 99% by mass or less relative to a total amount of the propylene-based polymer and the styrene-based elastomer, and
   a content of the styrene-based elastomer is 1% by mass or more and 10% by mass or less relative to the total amount of the propylene-based polymer and the styrene-based elastomer.

2. The polypropylene resin composition according to claim 1, wherein the hindered amine light stabilizer is a polymer containing a repeating structural unit having a secondary amino group.

3. The polypropylene resin composition according to claim 1, further comprising (E) a hydroxylamine compound having a hydroxylamino group.

4. The polypropylene resin composition according to claim 1, wherein a content of the monomer unit derived from ethylene in the propylene-based polymer is less than 5% by mass based on a mass of the propylene-based polymer.

5. A molded body for medical use consisting of the polypropylene resin composition according to claim 1.

6. A syringe comprising a barrel having the molded body for medical use according to claim 5.

7. A dialyzer comprising a housing having the molded body for medical use according to claim 5.

* * * * *